US00PP19313P3

(12) United States Plant Patent

Kerrigan et al.

(10) Patent No.: US PP19,313 P3

(45) Date of Patent: Oct. 14, 2008

(54) *AGARICUS SUBRUFESCENS* MUSHROOM PLANT NAMED 'H1X1'

(50) Latin Name: *Agaricus subrufescens Peck*
Varietal Denomination: H1X1

(75) Inventors: Richard W. Kerrigan, Kittanning, PA (US); Mark P. Wach, Allison Park, PA (US)

(73) Assignee: Sylvan Bioproducts, Inc., Kittanning, PA (US)

( * ) Notice: Subject to any disclaimer, the term of this patent is extended or adjusted under 35 U.S.C. 154(b) by 169 days.

(21) Appl. No.: 11/435,005

(22) Filed: May 15, 2006

(65) Prior Publication Data

US 2007/0266468 P1 Nov. 15, 2007

(51) Int. Cl.
*A01H 5/00* (2006.01)

(52) U.S. Cl. ..... Plt./394

(58) Field of Classification Search ..... Plt./394
See application file for complete search history.

(56) References Cited

U.S. PATENT DOCUMENTS 5,684,228 A * 11/1997 Kerrigan et al. ..... 800/266
6,378,244 B1 * 4/2002 Iwata et al. ..... 47/1.1

OTHER PUBLICATIONS

Rick Kerrigan–Composters Like it Hot !Dec. 1983, pp. 35–39; 65–67.

Richard W. Kerrigan–History and Biology of *Agaricus subrufescens*, Sep. 1983, pp. 313–319.

Maryna Ya. Didukh, Solomon P. Wasser and Eviator Nevo–Lectrotypification of the Name Agaricus Subrufexcens Peck (Agaricaceae, Higher Basidiomycetes)–2003, pp. 494–500.

Solomon P. Wasser, Maryna Ya. Didukh, Maria Angela L. de Amazonas, Eviator Nevo, Paul Stamets & Augusto F. de Eira–Is a Widely Cultiavted Culinary–Medicinal Royal Sun Agaricus (Champignon do Brazil, or the Himematsutake Mushroom) Agaricus brasiliensis S. Wasser et al. Indeed a Synonym of A. subrufescens Peck!

Solomon P. Wasser, Maryna Ya. Didukh, Angela L. de Amazonas, Evitator Nevo, Paul Stamets & Augusto F. de Eira–Is a Widely Cultiavted Culinary–Medicinal Royal Sun Agaricus (the Himematsutake Mushroom) Indeed Agaricus blazei Murrill!, 2002, pp. 267–290.

Richard W. Kerrigan–The Agaricales (Gilled Fungi) of California, 1986, p. 51.

Peck, C.H. –Report of the State Botanist, 1893, pp. 105–106, 135.

Richard W. Kerrigan–Agaricus subrufescens, a cultivated edible and medicinal mushroom and its synonyms, May 18, 2005, pp. 12–24.

* cited by examiner

*Primary Examiner*—Annette H Para
(74) *Attorney, Agent, or Firm*—Renner, Kenner, Greive, Bobak, Taylor & Weber

(57) ABSTRACT

A new and unique variety of the mushroom *Agaricus subrufescens* Peck was produced by crossbreeding a single spore isolate from the fungal strain 'I-101' and a single-spore isolate from the fungal strain 'SBRFG'. The resultant hybrid, named 'H1X1', exhibits early cropping, large size, high productivity, and an attractive appearance that includes a smooth, round cap.

1 Drawing Sheet

Latin name of genus and species: *Agaricus subrufescens* Peck.

Varietal denomination: 'H1X1'.

BACKGROUND OF THE INVENTION

The present invention relates to a new and distinct variety of mushroom plant of *Agaricus subrufescens* Peck. The present plant is an edible mushroom.

*Agaricus subrufescens* was first described in 1893 by C. H. Peck, the New York State Botanist, from mushrooms being cultivated in a greenhouse in Dosoris, N.Y., and some additional specimens found growing in the woods nearby. The mushroom, nicknamed the 'almond mushroom' due to its fragrance and taste, was widely cultivated, sold, and eaten in the Atlantic states of the United States of America from at least Massachusetts to Washington, D.C. in the latter years of the 19$^{th}$ century. Spawn (i.e., inoculum culture for farming) of *Agaricus subrufescens* was even offered for sale in catalogs of the day. Subsequently, commercial production of *Agaricus subrufescens* declined as market trends changed, and by the 1920–1930 period, virtually the only mushroom species being cultivated in the United States was the related 'button mushroom' species, *Agaricus bisporus* (Lange) Imbach. *Agaricus subrufescens* mushrooms have occasionally been found growing wild outside of northeastern North America in place such as, for example, California, Israel, and Hawaii. The recently described mushroom *Agaricus rufotegulis* Nauta from the Europe is, based on ITS1+2 and other DNA sequences, actually *Agaricus subrufescens,* and the same is true of the mushroom *Agaricus brasiliensis* Wasser et al. from South America.

The history of the mushroom *Agaricus subrufescens,* as well as a discussion of its properties as an easily cultivated mushroom has been reviewed and present by Kerrigan, one of the inventors of record, in several different articles circa 1983–1984. A culture of *Agaricus subrufescens* was isolated by Kerrigan from soil in California in 1982 and was subsequently sold commercially to hobbyist mushroom growers. Reproductive mode(s) and genetic behavior of this strain were investigated by Kerrigan and Ross (1987), and Kerrigan (2005).

*Agaricus subrufescens* mushrooms have more recently begun to be cultivated again on a wide scale, particularly in Brazil and Japan, as a 'medicinal mushroom' that is marketed primarily in Japan. However, in this context, the mushroom is typically referred to (incorrectly) as (1) *Agaricus blazei* Murr., (2) *Agaricus blazei* Marr. sensu Heineman, (3) *Agaricus sylvaticus,* or the recently coined (4) *Agaricus brasiliensis*. However, the data presented below and in Kerrigan, "*Agaricus subrufescens,* a cultivated edible and medicinal mushroom, and its synonyms," *Mycologia,* 97(1), May 18, 2005, pp. 12–24, the disclosure of which is incorporated herein by reference, indicate that the medicinal mushroom from Brazil and Japan is biologically and phylogenetically the same species as *Agaricus subrufescens* from North America. As Peck's species name *Agaricus subrufescens* is older than either *Argaricus brasilensis* or *Agaricus rufotegulis,* it has a nomenclatural priority under the International Code of Botanical Nomenclature and is therefore the correct name of the species. Therefore, the name *Agaricus subrufescens* is used herein inclusively. The species name applies not only to phylogenetically congruent isolates and specimens from all parts of the world but also to hybrids between them.

Cultivated material of *Agaricus subrufescens* was obtained from California, Brazil, Japan, and China. Hybridization (crossing) experiments were performed on selected pairs of stocks. When single-spore isolates (SSIs) from two different stocks are successfully crossed, the resulting hybrid incorporates genetic material from both progenitors, and the traits inherited from the parents may exist in a novel combination, or be intermediate in their nature. The successful production of hybrids strongly supports treatment of the parental isolates as members of a single species, regardless of their origin.

Furthermore, rDNA ITS1+2 sequences from many strains of *Agaricus subrufescens* were obtained from North America, South America, Europe, and Hawaii. It has been observed that *Agaricus subrufescens* has a considerable degree of cultural and morphological variability, but this variability is not vastly greater than in other species of *Agaricus* including *Agaricus bisporus.* It has also been found that the DNA sequences of diverse *Agaricus subrufescens* cultures are either identical or extremely similar, as is typically the case within other species of *Agaricus,* and share characteristics polymorphisms not known from other species. Thus, molecular markers have been developed that identify the species, identify strains within the species, and document the transmission of hereditary material from parental strains into offspring.

SUMMARY OF THE INVENTION

The present invention is a new and distinct variety of *Agaricus subrufescens* mushroom characterized by its rapid growth, high productivity, robust size and stature, and smooth round cap. That is, the present mushroom plant may be characterized by early and abundant production of mushrooms which are large and fleshy, with smooth, rounded caps. The new mushroom also has a genotype that combines markers from each of its progenitors. This novel and distinct variety of mushroom is identified as a *Agaricus subrufescens* hybrid mushroom named 'H1X1'. This new hybrid mushroom variety was produced in the breeding program of Sylvan Research, 198 Nolte Dr., Kittanning, Pa. 16201, by crossbreeding a single-spore isolate from the fungal strain 'I-101' and a single-spore isolate from the fungal strain 'SBRFG'.

The *Agaricus subrufescens* mushroom has been asexually reproduced by means of mycelial propagation in Kittanning, Pa. The resulting transfer culture (or 'subculture') is a common method for maintaining a mushroom strain on suitable media. Media such as PDA or MEA can be used as the mushroom culture media and the strain can be subcultured as frequently as every two or three weeks. To vegetatively propagate the mushroom culture aseptically, under laboratory conditions, a small portion of a pure (=axenic) culture on a suitable medium, such as potato dextrose agar (PDA), is transferred to a fresh plate or tube of newly prepared, sterilized medium (for example PDA) using a sterilized instrument such as a scalpel. Any aseptic transfer of an axenic culture to fresh culture medium achieves the objective of vegetative propagation. These techniques are standard and absolutely routine in the mushroom cultivation industry.

DESCRIPTION OF THE FIGURE

FIG. 1 is a photograph showing a front view of a culture of the present mushroom plant variety *Agaricus subrufescens* 'H1X1' growing on a substrate of composted straw. The tallest mushroom rises about 5 inches above the soil layer that covers the compost.

DETAILED DESCRIPTION OF THE INVENTION

In mushroom breeding, mycelial (=vegetative) cultures of two compatible progenitors must come into physical contact so that one or more fusion zones can occur between the progenitors. Within those fusion zones nuclei and organelles from the two progenitors become associated. In the better-studied *Agaricus bisporus,* a novel, hybrid mycelium ultimately containing two compatible haploid nuclear types and one mitochondrial type emerges. This novel hybrid mycelium can be isolated and propagated to provide the new hybrid culture, which can be further subdivided and propagated for commercial or other purposes.

In the genus *Agaricus* several reproductive modes exist, including outcrossing (=heterothallism), inbreeding/selfing (=pseudohomothallism), and haploid reproduction (=homothallism). More than one system can exist within species or even within isolates. In the latter case, the system is said to be amphithallic. Based on preliminary studies, *Agaricus subrufescens* appears to be an amphithallic species, meaning that spores released by the mushroom may carry one nuclear type (=haploid spores) or two nuclear types (=heterokaryotic spores). Either type can participate in hybridizations.

For the present variety, single spores were isolated and germinated from two examples of *Agaricus subrufescens,* those being (1) 'I-101', a single-spore isolate obtained from material cultivated in Japan, allegedly from strain Iwade-101, which strain was reportedly developed in Japan from Brazilian germ plasm, and (2) 'SBRFG', a subculture of the isolate made by Kerrigan in California in 1982. These single-spore isolates (=SSIs) were then propagated in broth and subjected to allozyme analysis. Segregation of alleles at the PEP1 and PEP2 loci were observed in progeny of 'I-101', and at an Esterase locus in 'SBRFG'. This demonstrates that meiosis, recombination and partitioning of recombination nuclei into spores is occurring in these isolates of *Agaricus subrufescens,* therefore is species is not homothallic. Furthermore, some SSIs had heteroallelic genotypes, providing that multiple nuclei were present in heterokaryotic spores, while other spores were homoallelic, implying that they could be homokaryotic. All of these observations are consistent with the presence of a basic system of amphithalillic reproduction in which outcrossing is possible.

Homoallelic SSIs were selected from the 'I-101' and 'SBRFG' stocks to be the progenitors of a series of hybrids. Crosses were made by placing inocula of two different SSIs, one from each parent stock, onto sterile nutrient media, and allowing the mycelia to grow into contact and fuse. Hybrid cultures were then isolated for each pairing.

The hybrid status of the putative new hybrids was verified by allozyme analysis. In the case of the new hybrid 'H1X1', the progenitor 'I-101'-s1 carries allele Pep2-s, while progenitor 'SBRFG'-s1 carries allele Pep2-f. The hybrid 'H1X1' between these two SSIs has the expected genotype Pep2-s/f, demonstrating that this isolate incorporates DNA from each parent. The simplest and most conventional explanation is that 'H1X1' received one nucleus from 'I-101'-s1 and another nucleus from 'SBRFG'-s1.

A set of 25 *Agaricus subrufescens* hybrids between parents 'I-101' and 'SBRFG' were grown on small containers of compost under standard conditions, with the 'SBRFG' parent added as a control. Hybrid 'H1X1' was one of only two hybrids to produce a crop after only 17 days, and was four days earlier than the 'SBRFG' parent. Hybrid 'H1X1' also had the highest yield, at 25% of the 'SBRFG' control, and 347% of the average of the 24 sibling hybrids. The properties of the mushrooms produced were also desirable, as described below.

The *Agaricus subrufescens* hybrid 'H1X1' differs from its parents in several economically important respects. In repeated tests 'H1X1' has rapidly produced an abundant crop of large mushrooms with smooth fleshy round caps. Neither the 'I-101'-s1, the 'SBRFG', nor the 'SBRFG'-s1 strains produce mushrooms with this combination of traits, whereas the 'H1X1' hybrid expresses this unique and desirable combination of traits from the two parents.

A comparison of those traits among members of this pedigree is provided in Table 1.

TABLE 1

Comparison of economically important traits in members of the pedigree of the 'H1X1' variety

| | Size/ | Trait | | |
|---|---|---|---|---|
| Strain | mass | Speed | Abundance | Cap shape |
| 'I-101'-s1 | 1x | Day x | 1x | Flat, smooth, thin |
| 'H1X1' | 3x-5x | Day x – 7 | 8-10x | Round, smooth, thick |
| 'SBRFG' | 3x-6x | Day x – 3 (–7) | 8-9x | Round, wrinkled, thick |
| 'SBRFG'-s1 | 3x-6x | Day x + 5 | 4x | Round, wrinkled, thick |

The size and mass (or weight) of a typical 'H1X1' mushroom is on average three to five times greater than that of an 'I101'-s1 mushroom, but is a bit smaller than the largest mushrooms from 'SBRFG'. The advantage of large mushrooms to the mushroom producer is that mushrooms of better perceived quality and higher value are produced, and these can be harvested more rapidly and at lower cost (per unit weight picked) than could a smaller mushroom.

Variety 'H1X1' typically produces a crop 7 days earlier than does 'I-101'-s1; this trait is also present in its 'SBRFG' parent. The yield (total weight) of a crop of 'H1X1' is typically 7–8 times as great as the crop produced by 'I-101'-s1, and may exceed that of 'SBRFG', after two flushes of mushrooms have been harvested. Taken together, these two traits means that the mushroom producer can produce a relatively larger crop in a shorter period of time, allowing extra crops to be planted each year.

The 'H1X1' hybrid has a very attractive cap combining the best qualities of the 'Iwade 101'-s1 and 'SBRFG parents. The round cap of 'H1X1' has more tissue mass and matures more slowly than the flat, thinner cap of 'I-101'-s1. The smooth cap surface of 'H1X1' is more attractive, remains cleaner and more free of soil-borne bacteria, and is easier the clean than wrinkled cap of 'SBRFG'. Therefore the crop of 'H1X1' has more value per unit weight because it is cleaner and requires less cleaning, has lower losses due to bacterial discoloration associated with soil trapped in wrinkles, and because its greater attractiveness creates a retail product that is more highly graded and priced.

A formal description of the mushrooms produced by variety 'H1X1' follows:

Pileus at harvest stage sub-spherical to hemispherical, 50–100 mm broad, smooth, covered with tiny (ca. 1 mm×1 mm) reddish brown (about dark Reddish Orange (RHS 175A–175C)) appressed scales on a whitish background. Flesh ca 10 mm thick. Lamellae free, close, initially whitish, becoming pinkish (about Pale Yellowish Pink (RHS 159C–159D)), light brown (about Yellowish Gray (RHS 156A)), and ultimately dark chocolate brown (Dark Red (RHS 187A) to Dark Grayish Reddish Brown (RHS200A) or more black) as maturation progresses. Veil forming a broad, elastic, pendant white annulus, semi-smooth above, floccose below, remaining attached to pileus margin well into maturation, leaving appendiculate remnants after dehiscence. Stipe white, smooth, subequal, 20–25 mm broad above, 30–40 mm broad below, by 8–15 cm long, base attached by mycelial cords, interior stuffed hollow; all parts becoming slightly to moderately yellow (about Light Yellow (RHS 16D) or more pale) when bruised, crushed or cut. Odor of almond extract. Chemical reactions and microscopic features are as previously described in Kerrigan, "*Agaricus subrugescens,* a cultivated edible and medicinal mushroom, and its synonyms," Mycologia, 97(1), May 18, 2005, pp.12–24, and in Kerrigan, *Agaricales of California* Vol. 6 Agaricacae. Arcata, Calif.: Mad River Press, pp.62, and as understood by those having ordinary skill in the art for the species *Agaricus subrufescens*.

What is claimed is:

1. A new and distinct variety of *Agaricus subrufescens* mushroom as substantially illustrated and described in the specification.

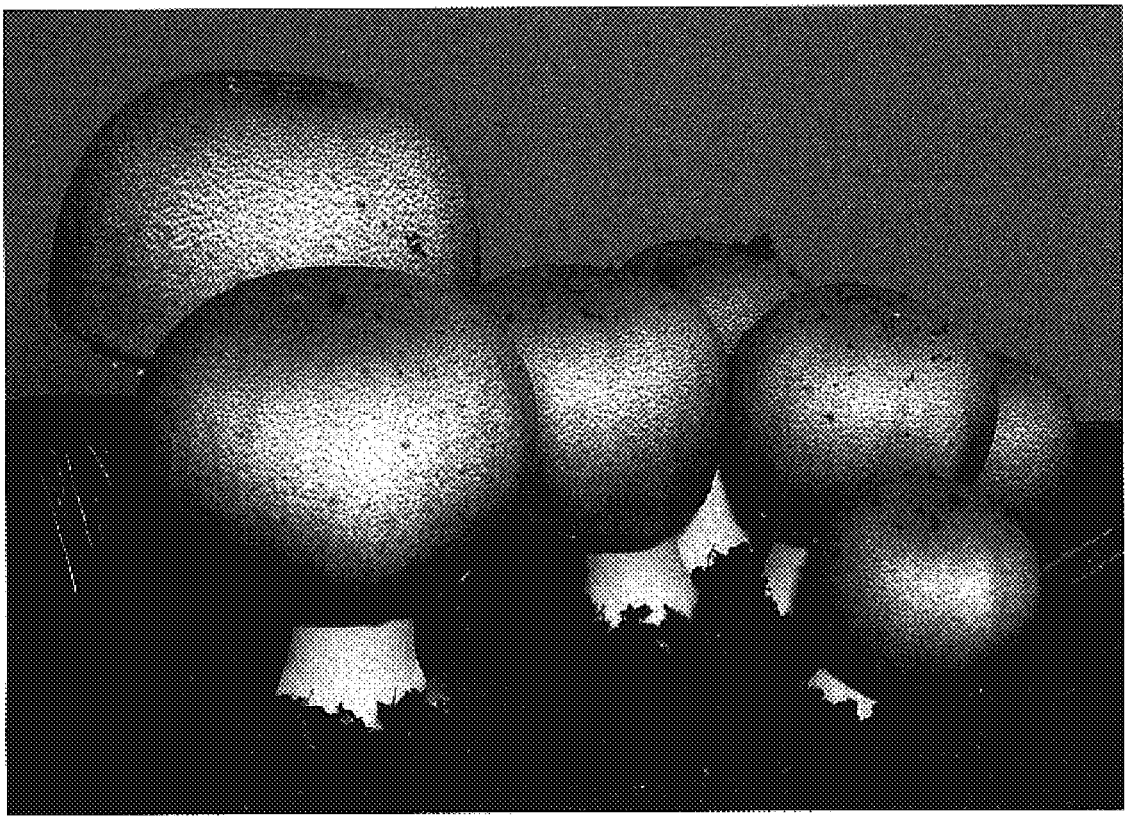

* * * * *